United States Patent [19]

Jones et al.

[11] Patent Number: 4,558,164

[45] Date of Patent: Dec. 10, 1985

[54] PRODUCTION OF DINITRODIPHENYL ETHER

[75] Inventors: Willard J. Jones, Pitman, N.J.; Thomas P. Gannett, Wilmington, Del.

[73] Assignee: E. I. Du Pont de Nemours and Company, Wilmington, Del.

[21] Appl. No.: 637,802

[22] Filed: Aug. 6, 1984

[51] Int. Cl.$^4$ .................. C07C 79/35; C07C 41/01
[52] U.S. Cl. .................................................. 568/585
[58] Field of Search .......................................... 568/585

[56] References Cited

U.S. PATENT DOCUMENTS 3,634,519  1/1972  Bentz et al. ...................... 568/585

FOREIGN PATENT DOCUMENTS 44-14334  6/1969  Japan .................................. 568/585

Primary Examiner—Bernard Helfin

[57] ABSTRACT

A process for preparing a symmetrical dinitrodiphenyl ether from o- or p-nitrochlorobenzene or o- or p-nitrofluorobenzene comprising using a polar organic solvent, a potassium salt of a fatty carboxylic acid containing 2 to 20 carbon atoms or a potassium salt of an aromatic carboxylic acid containing 7 to 12 carbon atoms as catalyst, and either sodium or potassium carbonate to react with the p-nitrochlorobenzene. The reaction is carried out at from 150° to 210° C. until the o- or p-nitrochlorobenzene or o- or p-nitrofluorobenzene reacts.

10 Claims, No Drawings

PRODUCTION OF DINITRODIPHENYL ETHER

BACKGROUND OF THE INVENTION

1. Field of the Invention

The present invention relates to a process for preparing symmetrical dinitrodiphenyl ethers from o- or p-nitrochlorobenzene or o- or p-nitrofluorobenzene.

2. Prior Art

Japanese published patent application No. 56-161354 discloses forming 4,4'-dinitrodiphenyl ether from p-nitrochlorobenzene using a polar organic solvent and a source of nitrite ions and an alkali metal salt of a fatty acid as a base.

The mechanism of the reaction is

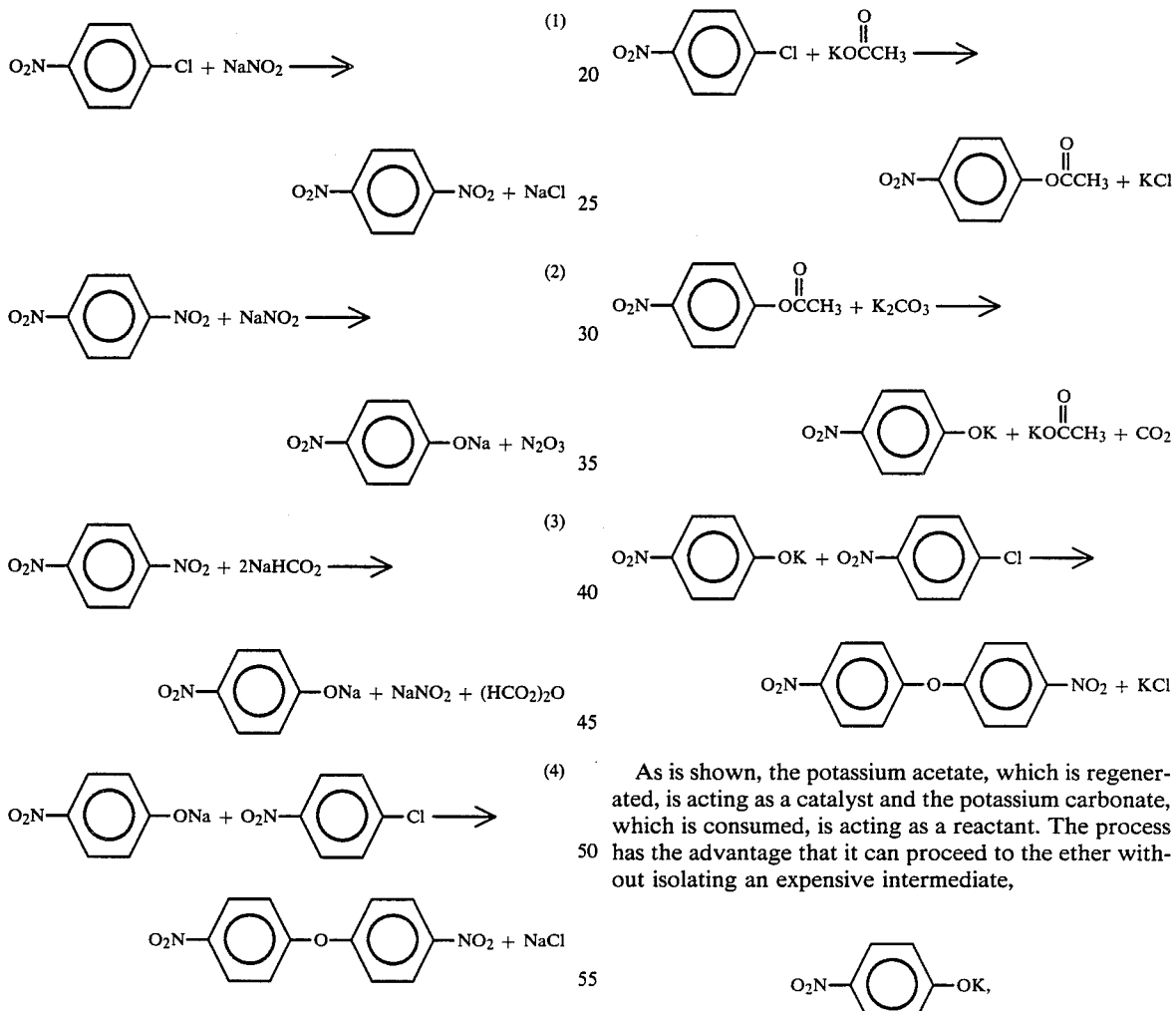

The production of 4,4'-dinitrodiphenyl ether via pathway (1) to (2) to (4) has been disclosed in the chemical journal literature since 1975*. Formation of p-dinitrobenzene is the slowest step, and it is an essential intermediate. A variety of bases have been claimed for step (3) Japanese published patent application No. 54-66633 discloses forming 4,4'-dinitrodiphenyl ether from p-nitrochlorobenzene using a polar organic solvent miscible with water, an alkali metal carbonate or acid carbonate, a source of nitrite ions, and water. Reaction (2) is simultaneous with reaction (3) and some sodium nitrite is always consumed. It is both a catalyst and a reagent, and as source of nitrite ion is always specified as an essential ingredient.

*Chemistry Letters, pages 1253–1256, published by Chemical Society of Japan (1975).

SUMMARY OF THE INVENTION

The present invention relates to a process for converting o- or p-nitrochlorobenzene or o- or p-nitrofluorobenzene into symmetrical dinitrodiphenyl ethers in a polar organic solvent using a salt of a carboxylic acid such as benzoic acid or acetic acid as a catalyst and potassium or sodium carbonate as reagents. Thus, the reaction of the present invention (when using potassium carbonate, acetic acid and p-nitrochlorobenzene) proceeds as follows:

As is shown, the potassium acetate, which is regenerated, is acting as a catalyst and the potassium carbonate, which is consumed, is acting as a reactant. The process has the advantage that it can proceed to the ether without isolating an expensive intermediate, while consuming an inexpensive reagent, i.e., potassium carbonate or sodium carbonate. The catalytic nature of the carboxylate is shown experimentally by its low mole ratio relative to p-nitrochlorobenzene (Example 1). Very little reaction occurs in the absence of the carboxylate catalyst (Example 2).

As further evidence for the mechanism and importance of the carboxylate anion and an alternate method of preparing dinitrodiphenyl ether, the following series of reactions takes place when only the salt of a carboxylic acid is heated with p-nitrochlorobenzene in dimethylacetamide.

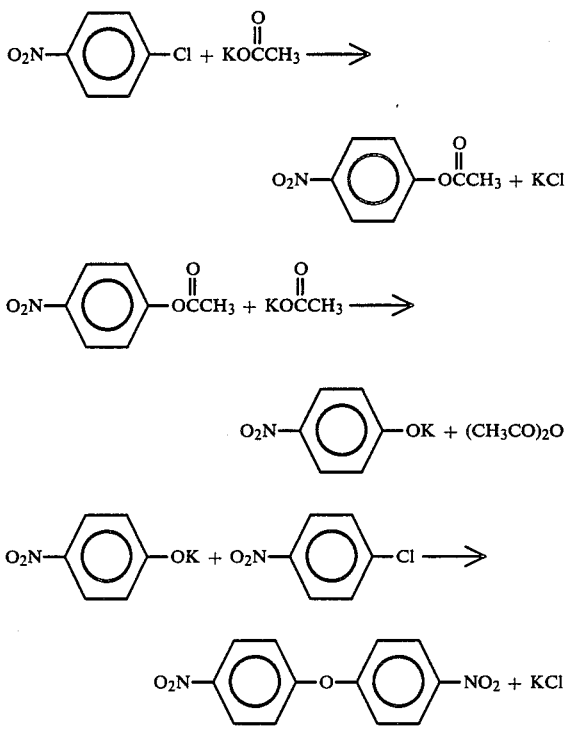

Both p-nitrophenyl acetate and dinitrodiphenyl ether are produced and can be isolated (Example 8).

DETAILED DESCRIPTION

The present invention relates to the preparation of symmetrical dinitrodiphenyl ethers which are useful in the manufacture of drugs, agricultural chemicals, synthetic resins, etc. For use in synthetic resins the nitro groups are reduced to amino groups to form a monomer which is then reacted with a diacid such as terephthalic acid or a dianhydride such as pyromellitic dianhydride.

The solvents used in the present invention are aprotic polar organic solvents such as dimethylacetamide, n-methylpyrrolidone, and dimethylsulfoxide. Generally the reaction is carried out at 150° to 210° C. with 190° to 210° C. being the preferred range. When using dimethylacetamide as the solvent, it generally boils in the range of 160° to 180° C. depending on the presence of the various reactants and products. Therefore, it may be necessary to carry out the reaction under pressure to prevent boiling of the solvent. The pressure used is not particularly critical, and while the minimum pressure of 20 to 30 psig ($13.8 \times 10^3$–$20.7 \times 10^3$ Pag) is necessary to maintain temperature and preferred for economic reasons, much higher pressures can be used. The concentration of the o- or p-nitrochlorobenzene or o- or p-nitrofluorobenzene in the aprotic polar solvent generally will be from 10 to 60 wt. % with 40 to 50 wt. % being the preferred range. The mole ratio of sodium or potassium carbonate relative to o- or p-nitrochlorobenzene or o- or p-nitrofluorobenzene is from 0.4 to 0.6. Generally about one half mole of sodium carbonate or potassium carbonate per mole of o- or p-nitrochlorobenzene or o- or p-nitrofluorobenzene will be present. Only aprotic polar solvents are useful, and dimethylacetamide is the preferred solvent. The reaction does not occur in protic solvents such as n-butanol (Example 6).

An aprotic polar solvent is a polar solvent which does not have a hydrogen available to dissociate or complex as in the case of an alcohol.

Catalysis by the carboxylate anion is not limited to p-nitrochloroöenzene, but will occur with any active halogen; in fact the fluoro derivative react faster than the corresponding chloro compound to give 4,4'-dinitrophenyl ether (Example 7). Also o-substituted nitrohalobenzenes can be used as starting materials to give 2,2'-dinitrodiphenyl ethers.

A sodium or potassium salt of a carboxylic acid selected from the group consisting of aromatic carboxylic acids containing from 7 to 12 carbon atoms and fatty acids containing from 2 to 20 carbon atoms are used as catalysts. Generally from 0.01 to 0.1 mole of carboxylic acid salt per mole of o- or p-nitrochlorobenzene or o- or p-nitrofluorobenzene will be present in the reaction mixture. Since the reaction medium is basic, the acid can be fed to the reaction medium and converted to the salt in situ.

EXAMPLES

EXAMPLE 1

A one liter autoclave fitted with an agitator is charged with 330 g (2.09 mole) p-nitrochlorobenzene, 273 g dimethylacetamide, 2.6 g (0.02 mole) benzoic acid and 112.2 g (1.06 mole) sodium carbonate. The reactor is purged with nitrogen and pressured to 30 psig with nitrogen. The reaction mixture is heated to and maintained at 210° C. while operating the agitator at 1000 rpm and keeping the pressure at 30 psig ($20.7 \times 10^3$ Pag). After 7 hours the reaction mixture is cooled to 125° C., the pressure released, and 200 g of dimethylacetamide removed by distillation at reduced pressure so as to keep the pot temperature $\leq 150°$ C. The reaction mixture is cooled to 130° C. and poured into 2 liters of hot water while agitating the mixture and keeping the temperature $\geq 95°$ C. The solids are filtered on a medium sintered glass funnal and washed with water at 95° C. After drying, the 4,4'-dinitrodiphenyl ether weighed 245 g (90% yield). The purity of the 4,4'-dinitrodiphenyl ether by gas chromotographic analysis is 99.7%.

EXAMPLE 2

The experiment of Example 1 is repeated except for the omission of benzoic acid; no carboxylate charged or produced in situ during reaction. The yield of 4,4'-dinitrodiphenyl ether is only 7% and the remainder is unreacted p-nitrochlorobenzene.

EXAMPLE 3

A one liter autoclave fitted with an agitator is charged with 200 g (1.27 mole) p-nitrochlorobenzene, 207 g dimethylacetamide, 6 g (0.03 mole) of potassium cyclohexanebutyrate, and 90 g (0.65 mole) of potassium carbonate. The reactor is purged with nitrogen and heated to and maintained at 200° C. under autogenous pressure while operating the agitator at 1250 rpm. After two hours the pressure levels off indicating completion of the reaction, no further elimination of carbon dioxide. The reaction mixture is cooled to 125° C. and drowned in hot water. After filtering and drying, the isolated 4,4'-dinitrodiphenyl ether weighs 145.6 g (88% yield).

EXAMPLE 4

A one liter autoclave fitted with an agitator is charged with 200 g (1.27 mole) p-nitrochlorobenzene, 377 g dimethylacetamide, 2.6 g (0.03 mole) potassium acetate, and 92 g (0.67 mole) potassium carbonate. The reactor is purged with nitrogen and heated to and maintained at 190° C. under autogenous pressure wnile agitating. After 4 hours the pressure leveled off and the reaction mixture is cooled to 125° C. It is then filtered to remove potassium chloride, and the 4,4'-dinitrodiphenyl ether in the filtrate is hydrogenated without isolation to 4,4'-diaminodiphenyl ether using hydrogen gas and a palladium catalyst. The overall yield of isolated 4,4'-diaminodiphenyl ether from p-nitrochlorobenzene is 70% and its m.p. is 189°–190° C.

EXAMPLE 5

A 500 ml flask equipped with an agitator, thermometer, and nitrogen bleed is charged with 157.5 g (1.0 mole) p-nitrochlorobenzene, 9.2 g (0.06 mole) potassium benzoate, 60 g (0.57 mole) sodium carbonate, and 100 g N-methylpyrrolidone. The reaction mixture is heated to and maintained at 200° C. while it is agitated and kept under a nitrogen blanket. After 7 hours the reaction mixture is cooled to 125° C. and drowned in 3 liters of water at 95° C. After filtration and drying, the 4,4'-dinitrodiphenyl ether weighs 110 g (85% yield).

EXAMPLE 6

A 250 ml shaker bomb is charged with 79 g (0.50 mole) p-nitrochlorobenzene, 43 g n-butanol, 3 g (0.03 mole) potassium acetate, and 30 g (0.28 mole) sodium carbonate. The reactor is purged with nitrogen and heated to and maintained at 200° C. under autogenous pressure for 9 hours. No increase in pressure is observed and no 4,4'-dinitrodiphenyl ether is formed. This example illustrates that the reaction will not proceed using a protic solvent.

EXAMPLE 7

A 250 ml flask equipped with an agitator, thermometer, and nitrogen bleed is charged with 66.5 (0.47 mole) p-fluoronitrobenzene, 77 g dimethylacetamide, 0.57 g (0.004 mole) potassium benzoate and 25 g (0.24 mole) sodium carbonate. The reaction mixture is heated to and maintained at 170° C. while it is agitated and kept under a nitrogen blanket. After 12 hours 4,4'-dinitrodiphenyl ether is obtained in 98.5% yield.

EXAMPLE 8

A one liter flask equipped with an agitator, thermometer, and nitrogen bleed is charged with 50 g (0.32 mole) p-nitrochlorobenzene, 510 g dimethylacetamide, and 10 g (0.10 mole) potassium acetate. The reaction mixture is heated to and maintained at 170° C. while it is agitated and kept under a nitrogen blanket. All the potassium acetate is consumed in an hour and the two products of the reaction are 4,4'-dinitrophenyl ether and p-nitrophenyl acetate, respectively, in a weight ratio of 1.5/1. This example illustrates the need to have either sodium carbonate or potassium carbonate present to form 4,4'-dinitrophenyl ether in high yield.

We claim:

1. A process for preparing a symmetrical dinitrodiphenyl ether from o- or p-nitrochlorobenzene or o- or p-nitrofluorobenzene starting material comprising forming a reaction medium wnich is a solution of 10 to 60% by weight o- or p-nitrochlorobenzene or o- or p-nitrofluorobenzene in an aprotic polar organic solvent said solution containing about 0.4 to 0.6 mole, per mole of o- or p-nitrochlorobenzene or o- or p-nitrofluorobenzene, of sodium carbonate or potassium carbonate and from 0.01 to 0.1 mole, per mole of o- or p-nitrochlorobenzene or o- or p-nitrofluorobenzene, of a sodium or potassium salt of carboxylic acid selected from the group comprising aromatic carboxylic acids containing from 7 to 12 carbon atoms and fatty acids containing from 2 to 20 carbon atoms, heating said reaction medium to from 150° to 210° C. to form symmetrical dinitrodiphenyl ether.

2. The process of claim 1 wherein the starting material is p-nitrochlorobenzene or p-nitrofluorobenzene.

3. The process of claim 2 wherein the solvent is dimethylacetamide.

4. The process of claim 2 wherein the catalyst is a salt of a fatty acid.

5. The process of claim 3 wherein the catalyst is potassium acetate.

6. The process of claim 5 wherein the carbonate is potassium carbonate.

7. The process of claim 2 wherein the catalyst is a salt of benzoic acid.

8. A process for preparing a symmetrical dinitrodiphenyl ether from p-nitrochlorobenzene comprising forming a reaction medium which is a solution of 40 to 50% by weight p-nitrochlorobenzene in dimethylacetamide, said solution containing about one half mole per mole of p-nitrochlorobenzene of sodium carbonate and from 0.01 to 0.1 mole per mole of p-nitrochlorobenzene of the sodium salt of benzoic acid, heating said reaction medium to from 160° to 180° C. to form symmetrical dinitrophenyl ether.

9. The process of claim 1 with the additional step of hydrogenating the symmetrical dinitrodiphenyl ether to form a symmetrical oxydianiline.

10. The process of claim 8 with the additional step of hydrogenating the symmetrical dinitrodiphenyl ether to form 4,4'-diaminodiphenyl ether.

* * * * *